US006634360B1

(12) United States Patent
Flodin (10) Patent No.: US 6,634,360 B1
(45) Date of Patent: Oct. 21, 2003

(54) DEVICE FOR SUPPLYING INHALATION GAS TO AND REMOVING EXHALATION GAS FROM A PATIENT

(76) Inventor: Björn Flodin, Tallåsvägen 8-10, Spånga (SE), 163 43

( * ) Notice: Subject to any disclaimer, the term of this patent is extended or adjusted under 35 U.S.C. 154(b) by 0 days.

(21) Appl. No.: 09/762,855

(22) PCT Filed: Sep. 2, 1999

(86) PCT No.: PCT/SE99/01517

§ 371 (c)(1),
(2), (4) Date: Feb. 14, 2001

(87) PCT Pub. No.: WO00/13730

PCT Pub. Date: Mar. 16, 2000

(30) Foreign Application Priority Data

Sep. 2, 1998  (SE) ............................................. 9802962

(51) Int. Cl.$^7$ ............................ A61M 16/00; A62B 9/06
(52) U.S. Cl. ............................. 128/207.14; 128/207.15
(58) Field of Search ..................... 128/204.18, 207.14, 128/207.15, 911

(56) References Cited

U.S. PATENT DOCUMENTS

| 2,854,982 A | * | 10/1958 | Pagano | 128/207.14 |
|---|---|---|---|---|
| 3,593,713 A | * | 7/1971 | Bogoff | 128/207.14 |
| 3,709,227 A | * | 1/1973 | Hayward | 128/207.15 |
| 3,788,326 A | * | 1/1974 | Jacobs | 128/207.15 |
| 3,880,168 A | * | 4/1975 | Berman | 128/207.14 |
| 4,170,232 A | * | 10/1979 | Khoury | 128/207.14 |
| 4,233,984 A | | 11/1980 | Walling | 128/207.14 |
| 4,246,897 A | * | 1/1981 | Muto | 128/207.15 |
| 4,327,720 A | * | 5/1982 | Bronson et al. | 128/207.15 |
| 4,423,725 A | * | 1/1984 | Baran et al. | 128/207.15 |
| 4,468,216 A | * | 8/1984 | Muto | 604/19 |
| 4,646,733 A | | 3/1987 | Stroh et al. | 128/207.16 |
| 4,840,172 A | * | 6/1989 | Augustine et al. | 128/207.14 |
| 4,850,371 A | * | 7/1989 | Broadhurst et al. | 128/207.14 |
| 4,892,095 A | * | 1/1990 | Nakhgevany | 128/207.14 |
| 5,067,497 A | * | 11/1991 | Greear et al. | 128/207.15 |
| 5,143,062 A | * | 9/1992 | Peckham | 128/207.14 |
| 5,185,007 A | * | 2/1993 | Middaugh et al. | 604/320 |
| 5,186,167 A | * | 2/1993 | Kolobow | 128/207.14 |
| 5,188,592 A | * | 2/1993 | Hakki | 604/35 |
| 5,188,622 A | * | 2/1993 | Muller et al. | 604/319 |
| 5,193,533 A | * | 3/1993 | Body et al. | 128/207.14 |

(List continued on next page.)

FOREIGN PATENT DOCUMENTS

| DE | 25 35 191 | | 2/1977 | |
|---|---|---|---|---|
| EP | 0 092 618 | | 11/1983 | |
| WO | WO97/37702 | * | 10/1997 | 128/207.15 |

*Primary Examiner*—Weilun Lo
*Assistant Examiner*—Joseph F. Weiss, Jr.
(74) *Attorney, Agent, or Firm*—Swidler Berlin Shereff Friedman, LLP (57) ABSTRACT

An integrated tracheal tube/suction ventilation and co-committal secretion removal device having first and second coaxially arranged conduits where the first interior conduit forms a lumen to deliver gas, and a circumferentially arranged second conduit lumen is structurally adapted to serve as an integral suction lumen for removal of both expiratory gases and secretions. The distal end outlets of both lumens terminate between the device's fixing member and its distal end. The two lumen outlets are arranged such that relative to each other and the device the first interior pipe conduit forming lumen's outlet is located at the distal end and the second pipe conduit lumen's outlet is located at or near the distal side of the fixing member. This selection of relative positioning facilitates optimal deliver of breathing gas to a user in conjunction with removal of expiratory gases and secretions. The device is sized for location of the fixing member to its distal end from a patient's carina to a patient's larynx.

24 Claims, 5 Drawing Sheets

U.S. PATENT DOCUMENTS

| | | | | |
|---|---|---|---|---|
| 5,255,675 A | * | 10/1993 | Kolobow | 128/204.18 |
| 5,291,882 A | * | 3/1994 | Makhoul et al. | 128/207.14 |
| 5,311,864 A | * | 5/1994 | Huerta | 128/207.15 |
| 5,372,131 A | * | 12/1994 | Heinen, Jr. | 128/207.15 |
| 5,456,250 A | * | 10/1995 | Hissong | 128/207.14 |
| 5,496,299 A | * | 3/1996 | Felix et al. | 604/319 |
| 5,542,937 A | * | 8/1996 | Chee et al. | 604/280 |
| 5,544,648 A | * | 8/1996 | Fischer, Jr. | 128/207.14 |
| 5,582,167 A | * | 12/1996 | Joseph | 128/207.15 |
| 5,605,149 A | | 2/1997 | Warters | 128/207.14 |
| 5,642,730 A | * | 7/1997 | Baran | 128/207.14 |
| 5,687,714 A | * | 11/1997 | Kolobow et al. | 128/207.14 |
| 5,819,723 A | * | 10/1998 | Joseph | 128/207.14 |
| 5,896,854 A | * | 4/1999 | Bliss et al. | 128/200.24 |
| 5,944,703 A | * | 8/1999 | Dixon et al. | 604/319 |
| 5,954,636 A | * | 9/1999 | Schwartz | 600/120 |
| 5,964,223 A | * | 10/1999 | Baran | 128/207.14 |
| 6,079,413 A | * | 6/2000 | Baran | 128/207.14 |
| 6,155,252 A | * | 12/2000 | Warters | 128/200.14 |
| 6,210,383 B1 | * | 4/2001 | Want et al. | 604/318 |
| 6,375,897 B1 | * | 4/2002 | Bachand | 422/58 |
| 6,391,009 B1 | * | 5/2002 | Crosa Dorado | 604/319 |
| 6,426,227 B1 | * | 7/2002 | Kritzman et al. | 436/43 |
| 6,460,540 B1 | * | 10/2002 | Klepper | 128/207.14 |

* cited by examiner

DEVICE FOR SUPPLYING INHALATION GAS TO AND REMOVING EXHALATION GAS FROM A PATIENT

THE BACKGROUND OF THE INVENTION AND PRIOR ART

The present invention refers to a device for supplying inhalation gas to and removing exhalation gas from a patient, including a pipe member, suited to be introduced into the trachea of a patient and comprising a first pipe conduit, which is intended for said inhalation gas and has a distal outlet opening arranged to be positioned at the dividing region of the main bronchi of the patient during use of the device.

The introduction of such devices for the supply of inhalation gas and the removal of exhalation gas, so called intubation, is made as a matter of routine in medical treatment of patients which need external breath support from a respirator. The device includes normally a plastic pipe, a so called endotracheal tube, which via the throat is guided down into the trachea to a position at the dividing region of the main bronchi. The endotracheal tube is fixed in the trachea by means of a fixing member which is provided slightly above the distal end of the tube and inflated to airtight abutment against the inner wall of the trachea. Air exchange, i e supply of relatively oxygen-rich inhalation gas and removal of exhalation gas, takes place through one single channel in the tube, which via an external manifold is connected to the supply outlet and removal inlet, respectively, of the respirator.

The body reacts in a natural way against foreign bodies and organisms, which are present in the airways, by an increased excretion of secretion from the mucous membranes in combination with an increased activity of the cilia. The purpose of the cilia is to catch and transport impurities and secretion out of the body by moving in such a way that they transfer an upwardly directed movement to these impurities and secretion.

When the tracheal tube is installed in the trachea, the cilia may not act any longer in the intended manner since the tracheal tube and the fixing member closes the natural transport way for the secretion, i e the natural cleaning system is by-passed. In addition, the tracheal tubes, which are used today, do not have a satisfactory capability of removing the secretion since the same quantity of gas is transported successively in both directions through the channel of the tracheal tube. Due to these two factors, the secretion and phlegm will be collected in the airways beneath the fixing member. In order not to completely close off the airways by phlegm and thereby prevent an efficient gas exchange, the airways has to be sucked continuously, typically in intervals of 2–3 hours night and days, to drain collected phlegm. Such suction drainage is performed by means of a catheter, which is guided down through the tracheal tube and which, by means of a sub-pressure, sucks secretion to a collecting container. However, suction drainage by means of a catheter is a process which is time-consuming and expensive, and frequently involves complications. Some usual such complications are injuries on the mucus membranes, infections by contamination of the lower respiratory tract, coincident alveoli in the lungs, acute oxygen deficit, heart disorder and unprepared extubation. In addition, the patient is subjected to significant stress, discomfort and a sense of suffocation. There are also other grounds frequently involving pneumonia due to the treatment by conventional endotracheal tubes. Since the fixing member is positioned far down in the trachea in order to minimise the exposure to the secretion producing surface of the trachea, secretion containing bacteria will remain above the fixing member. During exhalation it is not unusual with leakage at the fixing member, wherein contaminated secretion is drawn downwardly into the lungs during the subsequent inhalation.

U.S. Pat. No. 4,646,733 discloses an endotracheal tube which is intended to be used during high frequent respiratory treatment. The high frequent tracheal tube, which operates with air pulses in the frequency range 1–50 Hz, may be guided downwardly in a conventional tracheal tube to such a position that air pulses generated are guided into the bronchi. The trachea is in its extension by-passed in a conventional manner.

EP-A-92 618 discloses another type of endotracheal tube having an inner pipe conduit: which ha an expandable fixing member at its distal end, and having an outer pipe conduit, which is shorter than the inner pipe conduit and which also has an expandable fixing member at its distal end. The fixing member of the outer pipe conduit is arranged to fix the outer pipe conduit in the throat while the fixing member of the inner pipe conduit is arranged to fix the inner pipe conduit in the trachea or the gullet. The supply and removal of air always takes place through the same pipe conduit.

SUMMARY OF THE INVENTION

The object of the present invention is to overcome the problems mentioned above and provide an improved device for the supply of inhalation gas to and the removal of exhalation gas from a patient. In particular, it is aimed at an in this connection improved removal of secretion from the airways.

This object is obtained by the device initially defined, which in addition includes a second pipe conduit, which is intended for said exhalation gas and has an inlet opening provided above said outlet opening, and a fixing member, which is arranged to be introducable into the trachea and to enable fixing of said pipe conduits in the trachea, wherein the fixing member is arranged to be provided substantially immediately beneath the larynx of the patient and wherein the inlet opening of the second pipe member is provided substantially immediately beneath a fixing member and at a substantial distance from said outlet opening.

By such a device, the second pipe conduit, which removes the exhalation gas, will end just beneath the larynx, which allows the cilia in the trachea to operate substantially normally and thereby transport secretion upwardly towards the inlet opening of the second pipe conduit. The secretion which is excreted may thus, to a substantially higher degree than at conventional endotracheal tubes, be transported away together with the exhalation gases. This transport of secretion is also substantially facilitated by the fact that the device according to the invention includes two separate channels, one for the inhalation gas and one for the exhalation gas, and that the outlet for the inhalation gas has an orifice substantially distally with respect to the inlet for the exhalation gas. Hereby, an airflow in one direction is obtained in the pipe conduit as well as in the trachea, i e a closed flow circuit without so called "dead space". Also the gas exchange is more effective at the same time as impurities, in case of a possible leakage around the fixing member, are prevented from reaching the lungs by the upwardly directed airflow in the trachea. Furthermore, the fixing member is arranged to be positioned immediately beneath the larynx, which prevents secretion and phlegm from remaining in the trachea above the fixing member.

According to an embodiment of the invention, a distance member is provided around the first pipe conduit between said inlet opening and said outlet opening, and is arranged to ensure that the first pipe conduit is located at a distance from at least one part of an inner wall of the trachea. In such a manner a free passage is ensured for the exhalation gas and in addition the first pipe conduit is prevented from abutting the inner wall of the trachea, where it might have a negative influence on the function of the cilia. Advantageously, the distance member may include at least one resilient element, which is arranged to abut the inner wall of the trachea with an abutment surface which is significantly less than the area of the inner wall of the trachea. By such a resilient or elastic element, it is ensured that the distance member does not injure the inner wall of the trachea. Thanks to the relatively small abutment surface of the distance member, the cilia on the inner wall may be permitted to operate substantially unobstructed. According to an advantageous embodiment said element has a thread-like shape and extends in a helical-like. path. Thereby, the distance member may include several such thread-like elements, e g two, and in such a manner it is ensured that the first pipe conduit is positioned approximately centrally in the trachea. According the another advantageous embodiment, the distance member includes a net-like tubular structure arranged to abut the inner wall of the trachea.

According to a further embodiment of the invention, the first pipe conduit extends in the second pipe conduit. In such manner it is possible to preheat the normally colder inhalation gas by means of the warmer exhalation gas in an efficient manner. Thereby, the second pipe conduit may include at least two pipe portions, sector-shaped in cross section, which extend substantially in parallel to each other and are separated by means of a wall member. Furthermore, the fixing member may include an expansion body, which is arranged to be expandable to sealing abutment against the inner wall of the trachea by the supply of a medium. By such a fixing member, the pipe member may be fixed in a desired position immediately beneath the larynx, and in addition a substantially tight abutment against the inner wall of the trachea may be obtained.

According to a further embodiment of the invention, the second pipe conduit includes a collecting member, which is arranged at a distance from said inlet opening to be located outside the patient and which is arranged to collect liquid and particles from the exhalation gas. By such a collecting member it is possible to make the device closed i e the collected secretion does not need to come into contact with the environment and may be removed from the patient.

According to a further embodiment of the invention, a disinfectant is provided in the collecting member and arranged to be distributed successively in the collected liquid. Said disinfectant may advantageously be provided in a number of separate areas along a path, which extends from a lower region of the collecting member to an upper region thereof, wherein said disinfectant is arranged to be released concurrently with the rise of the level of the collected liquid in the collecting member.

According to a further embodiment of the invention, the collecting member includes a level indicator, which is arranged to indicate the liquid collected from the exhalation gas. In such a way, the personnel taking care of the patient may know if the collecting member is full and needs to be replaced. The level indicator may be, designed in different ways, e g it may include a medium which releases a colouring matter when it comes into contact with liquid.

According to a further embodiment of the invention, the second pipe conduit extends into the collecting member and includes an orifice in the collecting member, through which the liquid present in the exhalation gas may exit. Thereby, said orifice may be formed by a pipe portion of the second pipe conduit, which portion is designed to form an audible sound due to bubble formation during said removal when the level of the collected liquid reaches the pipe portion. Such a sound may also function as a level indicator, which facilitates the operation of the device. A well audible sound may be obtained if the pipe portion includes at least one slit, which extends from said orifice, and/or a perforation.

According to a further embodiment of the invention, the pipe member includes a first portion, which extends between said openings and the collecting member, and a second portion, which extends from the collecting member and is connectable to a respirator, wherein said first portion and second portions are releasably connected to the collecting member by means of at least one connecting member. In such a way replacement of the collecting member is facilitated. It is important that such a replacement may be performed quickly since the patient is not connected to the respirator when the collecting member is not connected.

According to a further embodiment of the invention, the pipe member is manufactured in a first material and includes at least one longitudinal portion, preferably two or several portions of a second material, wherein the second material has a higher shape permanence and a lower melting point than the first material. Advantageously, the portions of the second material are formed by strings moulded into the first material or one or several of the wall members. By such a structure of the pipe member, this may in a simple way be given the desired shape by being heated to a temperature in the proximity of the melting temperature of the second material and bent to the desired shape. Thereby, the pipe member may advantageously have a S-like extension above the fixing member.

BRIEF DESCRIPTION OF THE DRAWINGS

The invention is now to be explained more closely by means of a description of an embodiment and with reference to the drawings attached hereto, in which FIG. 1 discloses schematically a view of a device according to the invention, FIG. 2 discloses a cross-sectional view of a pipe member of the device along the line II—II in FIG. 1, FIG. 3 discloses a perspective view of a part of a pipe member of the device in FIG. 1, FIG. 4 discloses a part of a pipe member of the device with a distance member according to another embodiment, and FIG. 5 discloses details of the distance member according to the embodiment in FIG. 4.

DETAILED DESCRIPTION OF A PREFERRED EMBODIMENT OF THE INVENTION

Figure 1:
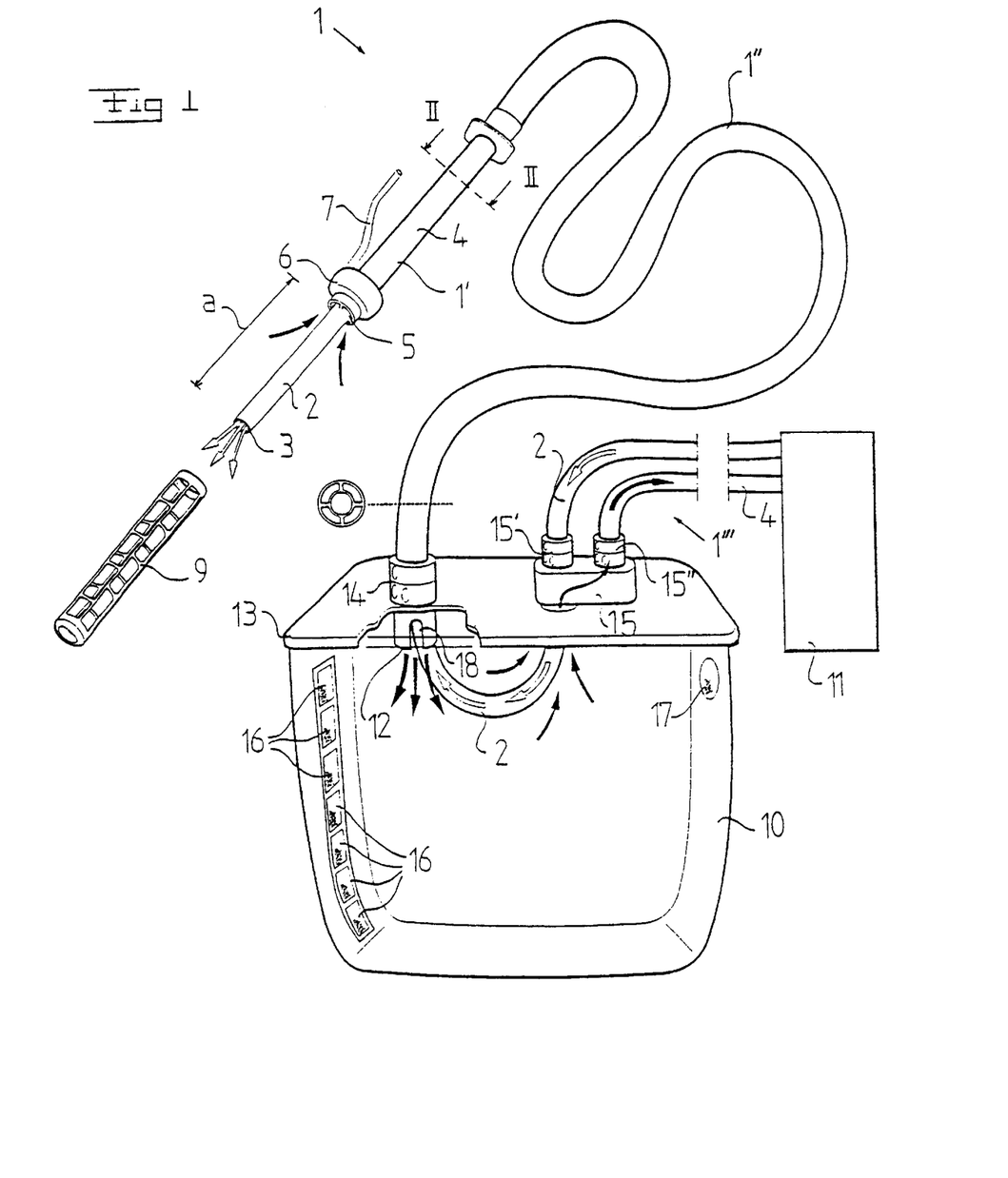

FIG. 1 discloses a device for the supply of inhalation gas to and the removal of exhalation gas from a patient. The device includes a pipe member 1 which is intended to be introduced into the trachea of a patient. The pipe member 1 includes a forward portion 1', which forms a so called endotracheal tube and which is intended to be located in the trachea and the throat of the patient, and a rearward portion 1", which may be connected to the forward portion 1' via a connecting member or be manufactured in one piece together with the forward portion 1'. In the embodiment disclosed, the rearward portion 1" is manufactured in a more flexible material than the forward portion 1'.

The pipe member 1 includes a first pipe conduit 2, which forms a first channel and is intended to transport said inhalation gas to the patient and which has a distal outlet opening 3 for the inhalation gas. Furthermore, the pipe member 1 includes a second pipe conduit 4, which forms a second channel and is arranged to transport said exhalation gas and which has an inlet opening 5 for the exhalation gas. As appears from FIG. 1, the outlet opening 3 is located at a distance a from the inlet opening 5, i e the outlet opening 3 is intended to be moved further downwardly into the trachea than the inlet opening 5, and more precisely to the dividing region of the main bronchi of the patient. Immediately above the inlet opening 5, a fixing member 6 is provided. The fixing member 6 includes a inflatable expansion body, which is arranged to be expandable to abutment against the inner wall of the trachea by the supply of a medium, preferably pressurised air via a conduit 7, which may be external or integrated in the pipe member 1. The fixing member 6 is intended to be positioned in the trachea immediately beneath the larynx of the patient, and consequently the distance a corresponds substantially to the distance from the lower end of the fixing member 6 to the dividing region of the main bronchi, i e the distance a is somewhat shorter than the length of the trachea beneath the larynx.

Figure 2:
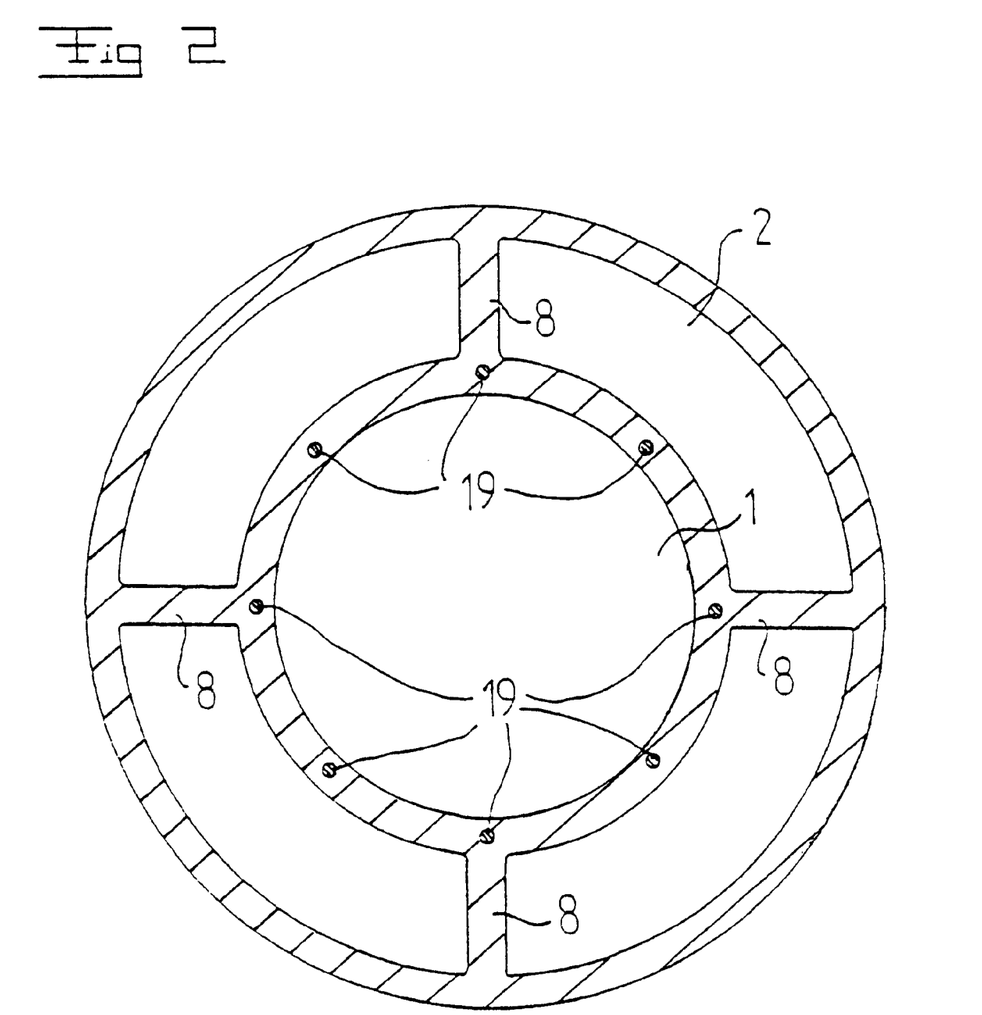

As appears from FIGS. 1 and 2, the first pipe conduit 2 is provided within the second pipe conduit 4 and advantageously the pipe conduits 2 and 4 are substantially concentric. It is to be noted that the cross-sectional area of the conduits 2 and 4 are somewhat less in the forward portion 1' of the pipe member 1 than in the rearward portion 1". The second pipe portion 4 includes four sector-shaped conduit portions, which extend substantially in parallel with each other and are separated from each other by means of wall members 8.

Figure 3:
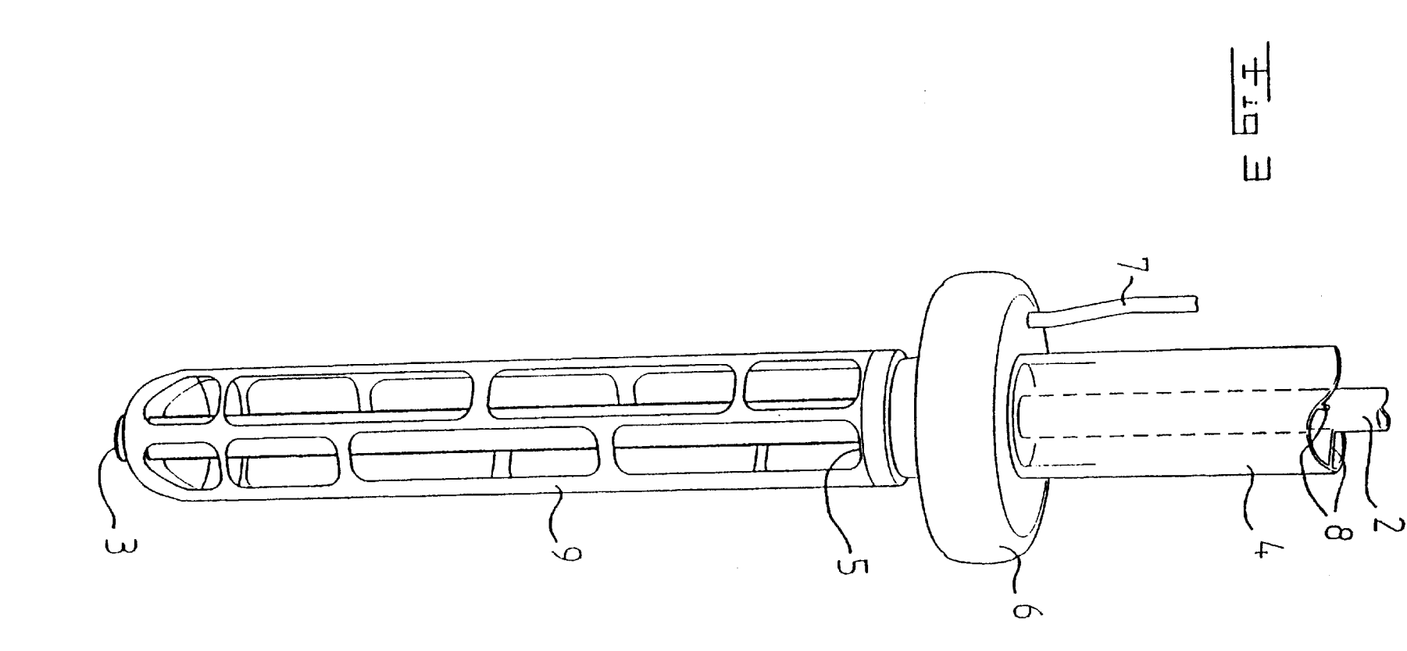

Furthermore, the device includes a distance member 9, 9', which is provided around the first pipe conduit 2 between the inlet opening 5 and the outlet opening 3. The distance member 9 has, according to the embodiment disclosed more closely in FIG. 3, a length which substantially corresponds to the distance a. The distance member 9 is arranged to ensure that the first pipe conduit 2 always is located at a distance from the inner wall of the trachea. The distance member 9 includes a resilient or elastic element which is designed as a cage which may be mounted onto the pipe member 1 and has a net-like structure with large measures or holes, i e the area of the measures exceeds substantially the area of the net-structure which forms the abutment surface of the distance member 9 against the inner wall of the trachea.

According to an alternative embodiment, the distance member may be formed by flanges extending in an axial and/or radial plain with respect to a longitudinal centre axis of the pipe conduit 2.

Figure 4:
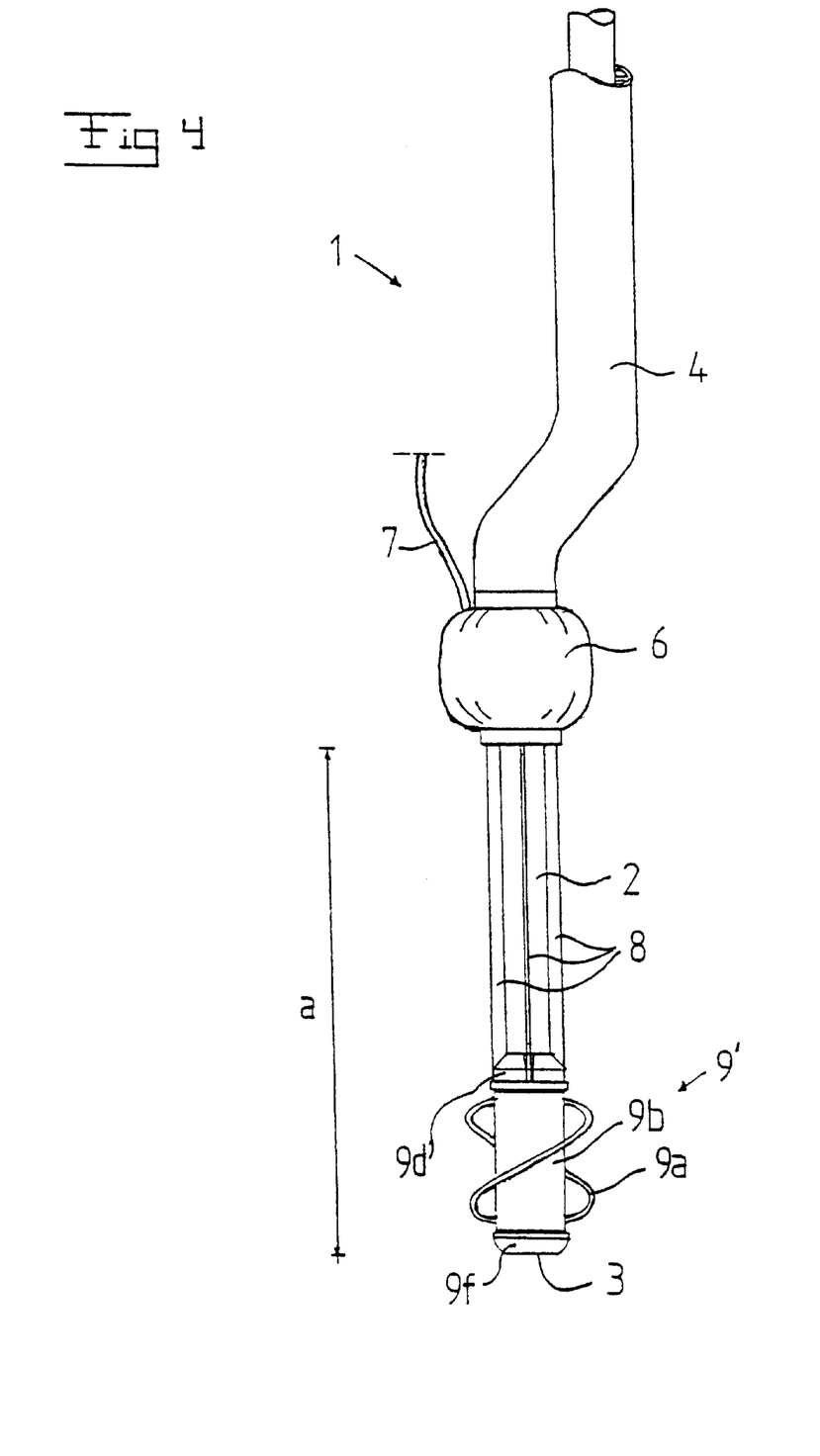
Figure 5:
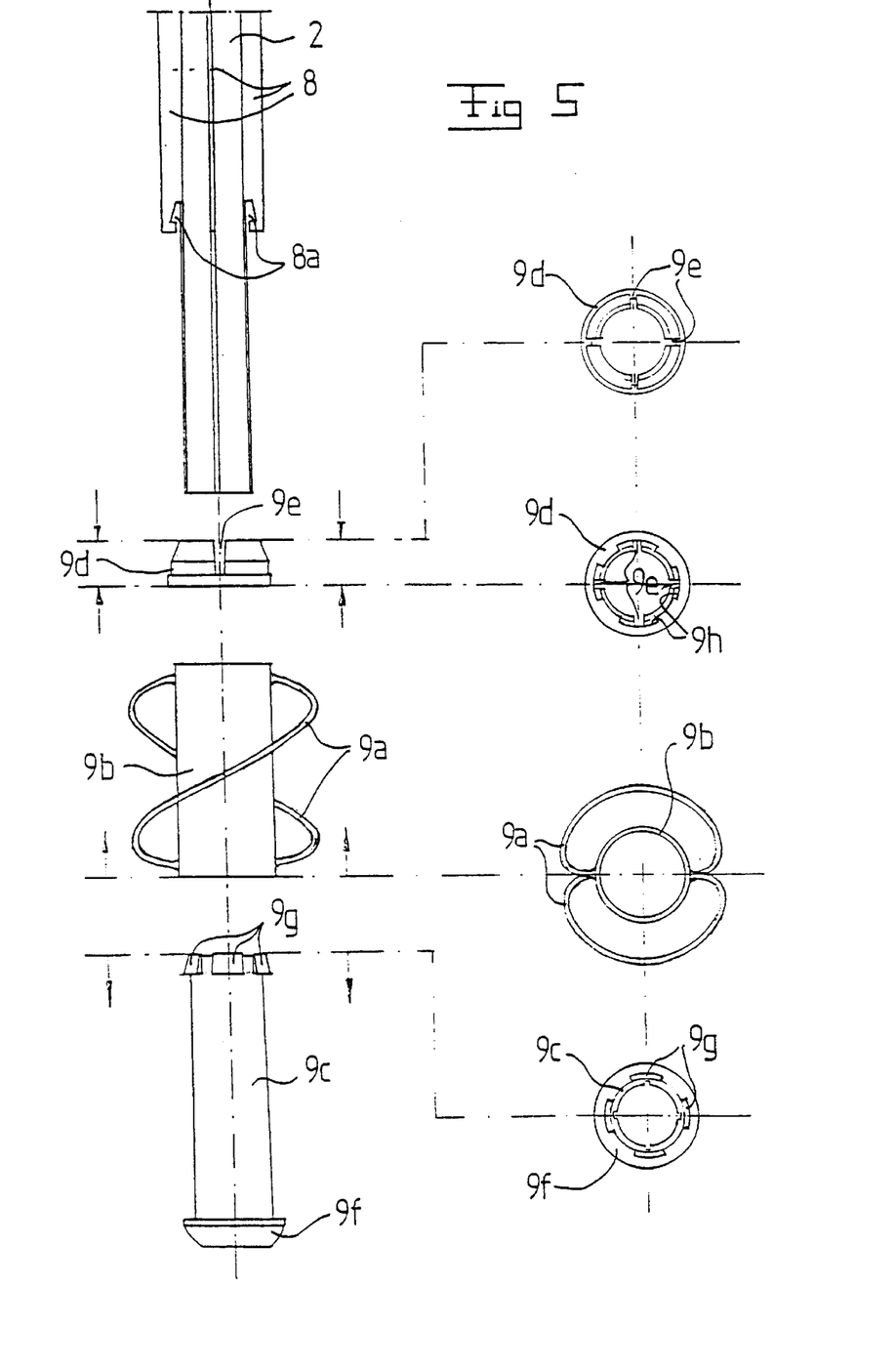

According to another embodiment disclosed more closely in FIG. 4, the distance member 9' extends from the distal opening of the first pipe conduit 2 towards the fixing member 6 along a smaller part of the distance a. The distance member 9" includes two, or possibly several resilient or elastic elements 9a, which have a thread-like shape and extends in a helical-like path with respect to a central axis through the first pipe conduit 2. In order to facilitate the introduction of the device into and retraction out of the trachea, the distance member 9' may be rotatable in relation to the first pipe conduit 2 and thereby include a central portion 9b, on which the resilient elements 9a are provided and which is rotatable in relation to a base portion 9c, see FIG. 5, which is fixedly provided on the first pipe conduit 2. The base portion 9c of the distance member 9' is arranged to be pushed onto the first pipe conduit 2 and maintained on the first pipe conduit 2 by means of an attachment portion 9d, which includes four grooves 9e extending in the longitudinal direction of the first pipe conduit 2 and being arranged to receive a respective wall member 8, which in this embodiment extends past the inlet opening 5. Each wall member 8 includes, in the lower part, a recess 8a. The central portion 9b is thus arranged to be provided on the base portion 9c in such a way that it may rotate. The central portion 35 9b is prevented from sliding off the base portion 9c by means of a flange 9f in the lower part of the base portion 9c. Furthermore, the attachment portion 9d is arranged to be mounted onto the base portion 9c above the central portion 9b and in such a way prevent the central portion 9b from sliding upwardly on the first pipe conduit 2. In the upper end, the base portion 9c includes four projections 9g which are arranged to extend through corresponding inner recesses 9h of the attachment portion 9d. Each wall member 8 includes in the lower part a recess 8a. When the base portion, 9c with the central portion 9b and the attachment portion 9d is pushed onto the first pipe conduit 2, the wall members 8 will slide in a respective groove 9e, wherein each recess 8a engages a respective projection 9g of the base portion 9c. In such a way it is ensured that the distance member 9' is maintained in a secure manner on the first pipe conduit 2 at the same time as the central portion 9b with the thread-like elements 9a is allowed to rotate.

Furthermore, the device includes a collecting member 10 in the form of a container which forms a part of the second pipe conduit 4. Consequently, the rearward portion 1" of the pipe member 1 is connected to the collecting member 10. Furthermore, the pipe member 1 includes a connecting portion 1'" which extends from the collecting member 10 to a schematically disclosed respirator 11. As mentioned above, the pipe conduits 2, 4 are concentric along the forward and rearward portions 1', 1" of the pipe member 1, while they are parallel but provided on a distance from each other in the connecting portion 1'" of the pipe member 1. Consequently, the second pipe conduit 4 has two orifices which are located in the interior of the collecting member 10. FIG. 1 discloses merely one 12 of these orifices since the orifice which is associated with the second pipe conduit 4 of the connecting portion of the pipe member 1 is hidden by a cover 13 of the collecting member 10. The exhalation air will thus be sucked from the inlet opening 5 by means of the respirator 11 through the second pipe conduit 4 and through the interior of the collecting member 10. Secretion, phlegm and possible impurities, which are present in the exhalation gas, will thus reach the interior of the collecting member 10 and be caught thereby. The first pipe conduit 2 also extends through the collecting member 10 without having any opening in its inner space, which means that the inhalation gas, delivered by the respirator 11, will be guided through the first pipe conduit 2 without any contact with the environment or the exhalation gas to the outlet opening 3 at the dividing region of the main bronchi.

The rearward portion 1" of the pipe member 1 is connected to the collecting member 10 by means of a first connecting member 14 which may be of a type including a snap or bayonet connection and which permits a quick release and attachment of the rearward portion 1" of the pipe member 1 to the collecting member 10 by a short turning movement. The connecting portion 1''' of the pipe member 1 is connected to the collecting member 10 by means of a second connecting member 15, which in the same way permits a quick release and attachment of the connecting portion 1'''. Thereby, the two pipe conduits 2 and 4 may be connected to a common connecting member 15 for both pipe conduits 2 and 4, or separately via two second connecting members 15', 15". According to a further embodiment, the rearward portion 1" and the connecting portion 1''' of the pipe member 1 may include a common connecting member which is connectable to and releasable from a connecting member of the collecting member 10. Furthermore, it is possible to design the collecting member between the rearward portion 1" and the forward portion 1' of the pipe member 1 in such a way that the rearward portion 1" is connected by its both ends to a respective opening of the collecting member 10. Therethrough, the collecting member 10 may during the whole post handling be kept substantially closed with respect to the environment. Preferably, the end of the rearward portion 1", which is connected to the forward portion 1' is arranged to be connected with one part of the connection of the connecting member 15 to the cover 13.

Advantageously, the collecting member 10 includes a disinfectant which is provided on an inner wall of the collecting member 10. The disinfectant may be provided in a number of separate areas 16 along a path or on a strip extending from a lower region of the collecting member 10 to an upper region thereof. In such a way, disinfectant will be released concurrently with the rise of the level of the collected liquid in the collecting member 10.

Furthermore, the collecting member 10 may include a level indicator 17, which is arranged to indicate the level of the liquid collected from the exhalation gas. The level indicator 17 may include a colouring matter which is bounded in a soluble manner in any substance and which is released from this substance when the liquid comes into contact with the substance and the colouring matter. In such a manner, the liquid in the collecting member 10 will be coloured by the colouring matter 17 when the liquid reaches the level at which the colouring matter 17 is located. The level in the collecting member 10 will also be indicated by the sound generated when the liquid reaches the orifice 12. Such a sound generation is amplified by means of holes or the disclosed slits 18 which extends upwardly from the orifice proper.

The forward portion 1' of the pipe member 1 is manufactured by extrusion or any similar method. Thereby, a first main material and a second material are utilised, which second material may be moulded in the first material as longitudinal strings 19, see FIG. 2. It is also possible to manufacture one or several, preferably two, of the wall members 8 of the second material. The second material has a higher shape permanence and a lower melting point than the first material. When the forward portion 1' of the pipe member 1 has been manufactured it may afterwards be heated to the melting point of the second material and bent to a desired shape. When it then is cooled down, the forward portion 1 will have the desired shape, see FIG. 4. Advantageously, the pipe member 1' above the fixing member 6, i e on the side of the fixing member 6 which faces away from the openings 3 and 5, may have a S-like extension, wherein the pipe member 1' extends along a straight line immediately above the fixing member 6, thereafter is bent to an extension which forms an angle to the straight line and then bent back to an extension which is substantially parallel to the straight line. In such a manner a shape is obtained which is anatomically adapted to the throat of a human being.

The device according to the invention may be employed in connection with intubation of human beings and animals via the throat and the trachea or via a cut through the trachea, so called tracheotomy.

The invention is not limited to the embodiment disclosed but may be varied and modified within the scope of the following claims.

What is claimed is:

1. A device operable to supply inhalation gas to and remove exhalation gas from a patient having a trachea, the device comprising:
   a first pipe conduit comprising an outlet opening operable to deliver inhalation gas to the patient;
   a second pipe conduit comprising an inlet opening surrounding a portion of the first pipe conduit and adapted to remove exhalation gas and secretions from the patient; and
   a fixing member interconnected with the device to fix the second pipe conduit in the trachea, the inlet opening of the second pipe conduit and the outlet opening of the first pipe conduit being distal to the fixing member, the relative positioning of the outlet opening and the inlet opening being selected to facilitate delivery of breathing gas to the patient in conjunction with removal of exhalation gas and secretions from the patient.

2. The device according to claim 1, wherein the pipe member comprises a first material and at least one longitudinal portion of a second material, wherein the second material has a higher shape permanence and a lower melting point than the first material.

3. The device according to claim 1, wherein the pipe member further comprises:
   an S-shaped extension arranged above the fixing member.

4. The device according to claim 1, wherein the inlet opening is positioned substantially immediately adjacent beneath the fixing member.

5. The device according to claim 1, wherein the inlet opening is positioned in the vicinity of the fixing member.

6. The device according to claim 1, wherein the outlet opening is operatively positionable at a dividing region of a main bronchi of the patient.

7. The device according to claim 1, wherein the fixing member is provided on the device to be operatively positionable substantially immediately adjacent beneath a larynx of the patient.

8. The device according to claim 1, wherein the first pipe conduit extends in the second pipe conduit.

9. The device according to claim 1, wherein the second pipe conduit further comprises at least two conduit portions having sector shaped cross-sections, and wherein the two conduit portions extend substantially parallel to each other and are separated by a wall member.

10. The device according to claim 1, wherein the fixing member comprises an expansion body operatively expandable into sealing abutment against the inner wall of the trachea by the supply of an inflating medium.

11. The device according to claim 1, further comprising:
   a distance member arranged around a portion of the first pipe conduit between the inlet opening and the outlet opening, and operable to ensure that the portion of the first pipe conduit is located at a distance from at least one part of an inner wall of the trachea.

12. The device according to claim 11, wherein the distance member comprises at least one resilient element including an abutment surface arranged to abut the inner wall of the trachea, wherein the abutment surface has significantly less than a surface area of the inner wall of the trachea.

13. The device according to claim 12, wherein the resilient element comprises a thread that extends in a path.

14. The device according to claim 11, wherein the distance member comprises a tubular net structure operatively positionable to abut the inner wall of the trachea.

15. The device according to claim 1, wherein the second pipe further comprises a collecting member that is arranged outside the patient at a distance from the inlet opening and operable to collect liquid and particles from the exhalation gas.

16. The device according to claim 15, further comprising:
   a disinfectant provided in the collecting member and arranged to be distributed successively in liquid collected in the collecting member.

17. The device according to claim 16, wherein the disinfectant is provided in a plurality of separate areas along a path extending from a lower region of the collecting member to an upper region thereof, wherein the disinfectant is arranged to be released concurrently with the rise of the level of the collected liquid in the collecting member.

18. The device according to claim 15, wherein the collecting member further comprises a level indicator operable to indicate liquid collected from the exhalation gas.

19. The device according to claim 18, wherein the level indicator includes a medium that releases a coloring matter when the medium comes into contact with the liquid collected from the exhalation gas.

20. The device according to claim 15, wherein the second pipe conduit extends into the collecting member and includes at least one of an orifice and a perforation in the collecting member, through which the liquid present in the exhalation gas can exit.

21. The device according to claim 20, wherein the orifice is formed by a pipe portion of the second pipe conduit, wherein the pipe portion is operable to generate an audible sound during collection of liquid from the exhalation gas when a level of collected liquid reaches the pipe portion.

22. The device according to claim 21, wherein the pipe portion includes at least one slit that extends from the orifice or the perforation.

23. The device according to claim 15, wherein the pipe member further comprises:
   a first portion that extends between the openings of the first pipe conduit and the second pipe conduit and the collecting member,
   a second portion that extends from the collecting member and is connectable to a respirator, and
   at least one connecting member operable to releasably connect the first portion and the second portion to the collecting member.

24. A device operable to supply inhalation gas to and remove exhalation gas from a patient, the device comprising:
   a pipe member operable to be introduced into a trachea of a patient, the pipe member comprising
      a first pipe conduit comprising an outlet opening operable to deliver inhalation gas to the patient;
      a second pipe conduit comprising an inlet opening surrounding a portion of the first pipe conduit and adapted to remove exhalation gas and secretions from the patient, wherein the second pipe conduit further comprises a collecting member arranged outside the patient at a distance from the inlet opening and operable to collect liquid and particles from exhalation gas; and
   a fixing member interconnected with the device to fix the second pipe conduit in the trachea, the inlet opening of the second pipe conduit and the outlet opening of the first pipe conduit being distal to the fixing member, the relative positioning of the outlet opening and the inlet opening being selected to facilitate delivery of breathing gas to the patient in conjunction with removal of exhalation gas and secretions from the patient.

* * * * *